United States Patent [19]

Parker

[11] Patent Number: 4,867,678

[45] Date of Patent: Sep. 19, 1989

[54] ORTHODONTIC BRACKET

[76] Inventor: Robert A. Parker, 83 Gilbert Road, Cambridge Cambridgeshire CB4 3NZ, England

[21] Appl. No.: 149,115

[22] Filed: Jan. 27, 1988

[30] Foreign Application Priority Data

Jan. 29, 1987 [GB] United Kingdom ............... 8701988

[51] Int. Cl.⁴ .................................................. A11C 7/00
[52] U.S. Cl. .......................................................... 433/8
[58] Field of Search ....................................... 433/16, 8

[56] References Cited

U.S. PATENT DOCUMENTS

| | | |
|---|---|---|
| 2,379,011 | 6/1945 | Laskin .................................... 433/16 |
| 3,423,833 | 1/1969 | Pearlman ............................... 433/16 |
| 3,721,005 | 3/1973 | Cohen .................................... 433/16 |
| 4,139,945 | 2/1979 | DiGiulio ................................ 433/16 |
| 4,219,617 | 8/1980 | Wallshein ............................... 433/8 |
| 4,597,739 | 7/1986 | Rosenberg ............................. 437/16 |

Primary Examiner—Robert Peshock
Attorney, Agent, or Firm—Wood, Herron & Evans

[57] ABSTRACT

The invention relates to an improved bracket for use in fixed dental appliances for the orthodontic movement of teeth. An orthodontic bracket in accordance with the invention comprises a fixed member for attachment to the labial surface of the tooth and a member which is freely rotatable about a stub axle formed in the fixed member, the rotatable member being provided on its labial surface with a first channel in which archwire may be seated, means being provided to lock the rotatable and fixed members together at a predetermined angular position. Such a bracket allows free tipping of the teeth in the early stages of treatment and allows torque to be applie for fine control of the root apices in the latter stages of treatment.

13 Claims, 3 Drawing Sheets

ORTHODONTIC BRACKET

The invention relates to an improved bracket for use in fixed dental appliances for the orthodontic movement of teeth.

There are two basic types of tooth movement which may be brought about by the use of fixed orthodontic appliances. These are described respectively as tipping and torqueing. Tipping is the simplest and quickest movement to carry out and is achieved by applying a force directly to the crown of the tooth such that the crown moves in the direction of the applied force and the root apex in the opposite direction. The fulcrum is established usually within the root of the tooth. Tipping can be either along an axis perpendicular to the outside plane of the tooth i.e. sideways, or along an axis parallel to the outside plane of the tooth.

Torqueing involves the controlled movement of the apices of the crown and roots of the teeth and is achieved by applying a force-couple to the crown in such a way that the fulcrum lies within the crown. Mesial or distal movement of the apices is referred to as uprighting.

Fixed appliances used to bring about tooth movement have three basic components, brackets, archwire and accessories. Brackets are rigidly attached to the tooth surface either, directly via a bonding interface, or to a band which is cemented to the tooth. They carry a channel into which archwire can be seated. The distal ends of the archwire are anchored to the molars by, for example, a buccal tube which itself is banded to the molars. Forces to the teeth may be generated either by the archwire itself or by accessories such as uprighting springs, rotation springs, coil springs or elastics.

Two popular techniques used to move teeth utilize different mechanical principles. They are the Begg technique and the Edgewise technique. Brackets used in the Begg technique have an archwire channel which is mesiodistally narrow, into which round archwire is loosely fitted and held by a locking pin. The narrowness of the bracket and the loose fitting wire allows free tipping of teeth to occur both around and along the archwire. Free tipping is advantageous in the early stages of treatment in that tooth movement is achieved rapidly, especially where teeth are grossly misplaced. The disadvantage is that apical movement must be brought about by uprighting springs and other accessories after free tipping has been allowed to occur. The fine control or apical movement brought about by torque and needed at the end of treatment for finishing is not easily achieved.

These disadvantages of the Begg technique are overcome using the edgewise system. Edgewise brackets are mesiodistally wide, having an archwire channel which is rectangular in cross-section. The archwire fits tightly into the channel so that free tipping along the wire is prevented. Tipping around the wire may also be prevented by the use of rectangular section archwire. Torque is applied to the teeth by means of twists, bends and loops in the archwire, as well as other accessories such as elastics. Edgewise brackets provide three-dimensional fine control of tooth movement and finishing is far superior to that obtained with the Begg technique. However, the absence of free tipping along the wire means that treatment is liable to take longer. Furthermore, the frictional resistance of the archwire means that to slide teeth along the wire, extra-oral traction is required in the form of headgear which is not favoured by patients.

Attempts have been made to introduce hybrid brackets containing both a free tipping channel for archwire and a non-tipping channel so that the advantages of free tipping in the early treatment are combined with steady control of the later stages similar to an edgewire bracket. These hydrid brackets have proved unsatisfactory since they have been found to be good at one technique or the other but, so far not good at both.

It is the aim of the invention to provide an orthodontic bracket which combines the two dental techniques currently used to move teeth, such that free tipping occurs in the early stages of treatment but is prevented in the later stages thus allowing fine control by means of torque to be applied to the teeth for satisfactory finishing.

In the following description the surface of the bracket adjacent the tooth surface is described as the lingual surface and the surface of the bracket adjacent the lips is described as the labial surface.

An orthodontic bracket in accordance with the invention comprises a fixed member for attachment to the labial surface of the tooth and a member which is freely rotatable about a stub axle formed in the fixed member, the rotatable member being provided on its labial surface with a first channel in which archwire may be seated, means being provided to lock the rotatable and fixed members together at a predetermined angular position.

The rotatable member preferably comprises a ring carrying on its labial surface, a rectangular flange which is traversed by the first channel and also by a second channel which is perpendicular to and approximately twice as deep as the first channel. The protruding corners of the rectangular flange may then provide means for retaining elastics.

The fixed member or base preferably has a third channel formed in the labial surface which is open to the second channel on the rotatable member. The second and third channels together therefore provide an open slot which can receive a locking member, e.g. the archwire, so that rotation of both the fixed and mobile members is prevented.

The base may also have on its lingual surface a fourth channel which may be perpendicular to the third channel, to receive an uprighting spring during the course of treatment.

In the course of orthodontic treatment the base of the fixed member is attached to the tooth by conventional means and the stub axle formed in the base supports the rotatable member. Archwire is seated in the first channel and forces are applied to the tooth by means of elastics and other accessories. As a result of such forces, the tooth may tip freely along the archwire due to the free rotation of the rotatable member about the stub axle. When a satisfactory degree of tipping has been achieved the archwire is disengaged from the first channel and the rotatable part turned through 90° so that archwire may be seated in the second channel which will, at this stage be out of alignment with third channel due to the angle of tip of the tooth. An uprighting spring is inserted in the base and connected to the archwire to facilitate movement of the root of the tooth into vertical alignment with the crown. When the tooth reaches its correct upright position the second channel will be aligned precisely with and open to the third channel thereby forming a deep slot into which the archwire slips so locking the rotatable and fixed parts and preventing further uprighting or free tipping. The device thereafter functions as an edgewise bracket with which additional accessories can be used to apply torque thereby facilitating finely controlled apical movement and good finishing.

An example of a bracket in accordance with the invention will now be described with reference to the accompanying drawings in which.

Figure 4:
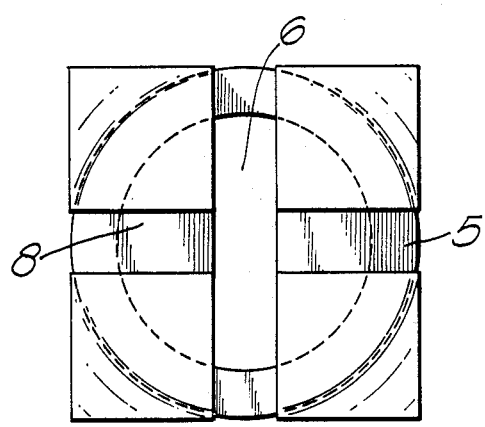
FIG. 4 is a front view of the rotatable member.
Figure 5:
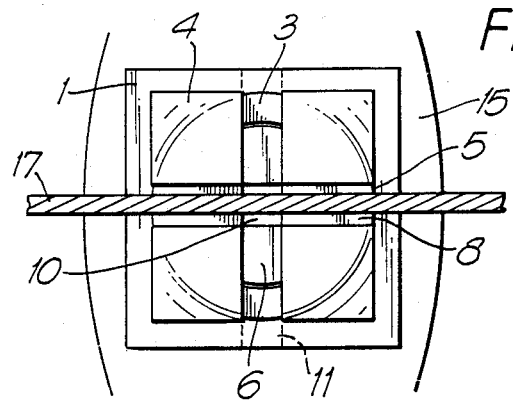
FIG. 5 is a front view of the bracket when fixed to the tooth with archwire engaged at the beginning of the treatment.
Figure 6:
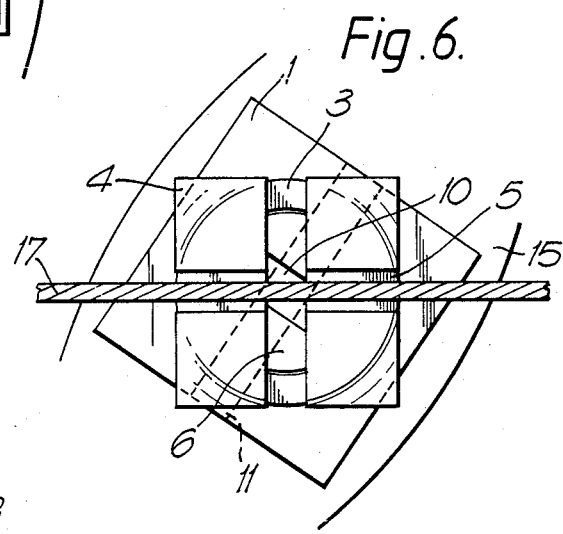
FIG. 6 is a view corresponding to FIG. 5 illustrating the position after tooth has tipped along the archwire.
Figure 7:
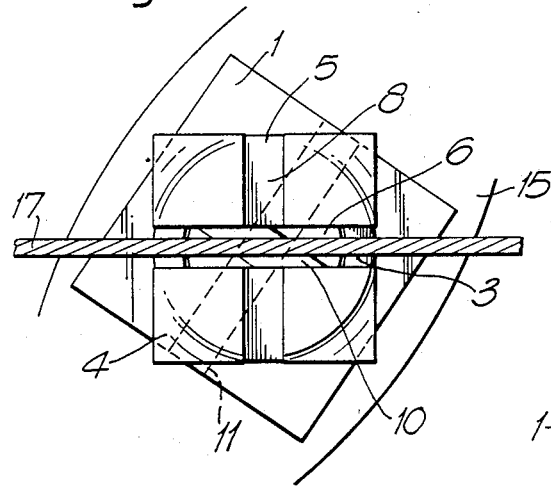
Figure 8:
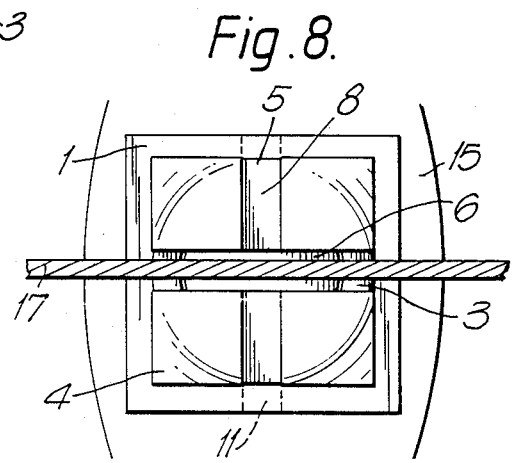

FIG. 7 is a view corresponding to FIGS. 5 and 6 illustrating the position where the rotatable member has been turned through 90° to seat the archwire in the second channel, and FIG. 8 is a view corresponding to FIGS. 4, 5 and 6 illustrating the position when the tooth is uprighted and the archwire engages the third channel.

Figure 1:
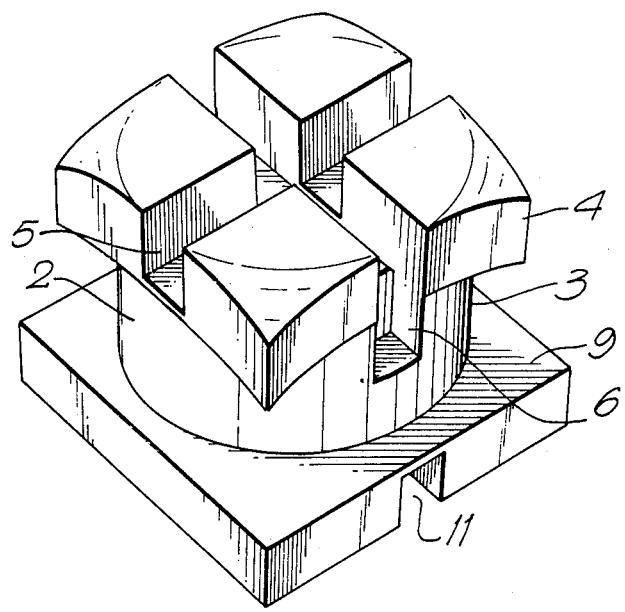
FIG. 1 is a perspective view of the bracket.
Figure 2:
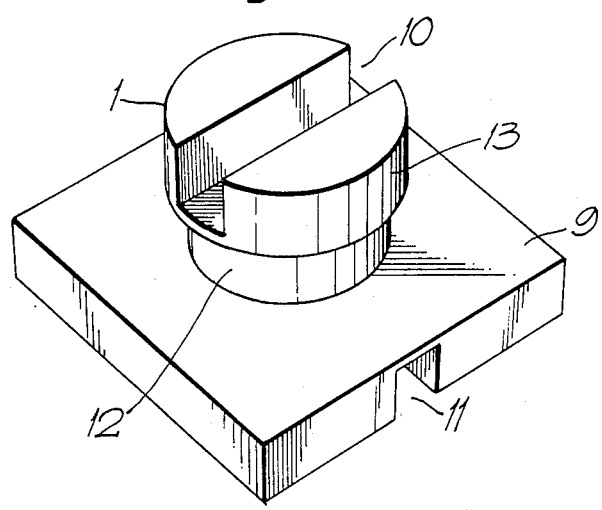
FIG. 2 is a perspective view of the base and stub axle portion of the bracket shown in FIG. 1.

Referring to FIGS. 1 and 2, the bracket comprises a fixed member 1 and a rotatable member 2. The rotatable member 2 comprises a ring 3 bearing on its labial side a rectangular flange the corners of which project over the outer circumference of the ring 3 and are curved in the lingual direction, as seen at 4.

The rectangular flange of the ring 3 is traversed by first and second channels 5 and 6 which are perpendicular to one another for the engagement of archwire, the second channel 6 being approximately twice as deep as the first channel 5. The first channel 5 is bounded at its lingual side by a wall 8 (shown in FIG. 4). The second channel 6, however is open at both the lingual and labial sides.

The fixed member 1 comprises of a rectangular base 9 provided with, on its lingual surface, a fourth Channel 11 and on its labial surface a stub axle 12, said stub axle having a head 13 in which is formed the third channel 10, perpendicular to the fourth channel 11.

Figure 3:
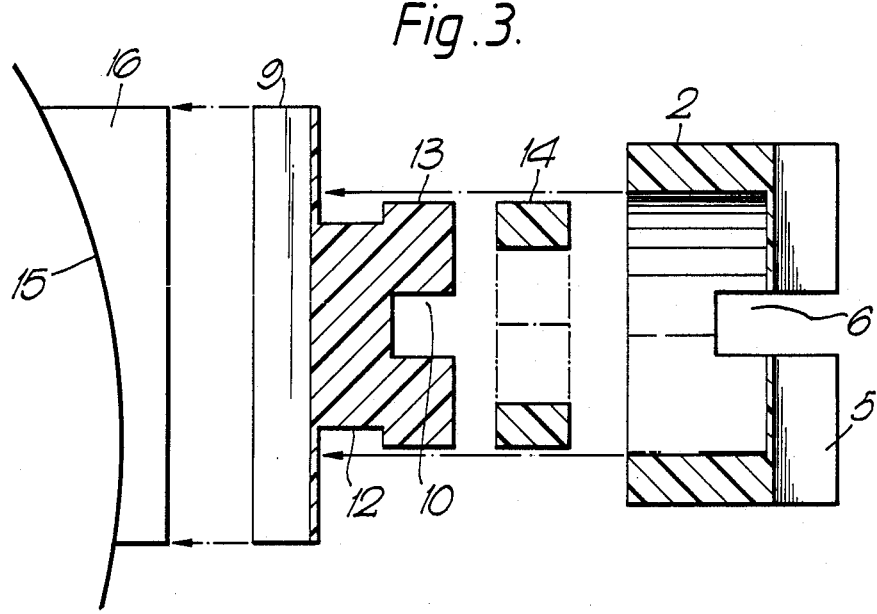
FIG. 3 is an exploded cross-sectional view of of the components of the bracket.

Referring now to FIG. 3, the ring 3 of the rotatable member 2 fits over the head 13 of stub axle 12 and is held there by means of a locking ring 14 thus preventing the rotatable member 2 and fixed member 1 from pulling apart. As an alternative to the locking ring, the ring 3 may be provided on its lingual side with a locking lip (not shown), which engages the stub axle 12. Once the ring 3 is engaged and held with the stub axle 12, by whatever means, the rotatable member 2 is free to rotate about stub axle 12 and head 13, through 360°.

The rectangular base 9 of the fixed member 1 may interface with tooth 15 via a contoured base portion 16 which is shaped to fit the tooth exactly.

The operation of the bracket will now be described with reference to FIGS. 5,6,7 and 8.

The base of the bracket 1 is fixed to the tooth 15 by conventional means and the rotatable member 2 rotated so that archwire 17 is seated in the first channel 5 as shown in FIG. 5. The archwire 17 is prevented from engaging in the third channel 10 by the wall 8 and thus the tooth 15 is free to tip along the archwire 17 by means of rotation of member 2 when forces are applied.

The relative positions of the fixed and rotatable members after free tipping has occured are shown in FIG. 6. When the degree of tipping is satisfactory the archwire 17 is disengaged from the first channel 5, the rotatable member 2 rotated through 90°, and the archwire 17 seated in the second channel 6 as shown in FIG. 7.

An uprighting spring may then be placed in the fourth channel 11 on the lingual surface of the base 9 and attached to the archwire 17 to bring the root of the tooth 15 into vertical alignment with the crown. When the tooth 15 reaches the correct position, shown in FIG. 8, the second channel 6 will precisely align with third channel 10 into which the archwire 17 slips so preventing the two components of the bracket from further rotation. Thus uprighting is terminated at the correct position automatically and further free tipping along the archwire is also prevented, the bracket having been effectively converted to an edgewise device by the locking mechanism. Such a bracket therefore combines the advantages of the Begg technique i.e. free tipping in the early stages of treatment, with the benefits of an edgewise bracket i.e. fine control of tooth apices, in the later stages. This device should simplify the choice of appliances for straightening teeth, lead to shorter treatment time and reduce the amount of discomfort suffered by the patient.

What we claim is:

1. An orthodontic bracket for moving a tooth first by tipping, second by uprighting and third, where necessary, by torquing, said bracket comprising
   a first member having a tooth attachment surface for attachment to a tooth's labial surface,
   a second member rotatably connected to said first member on an axis substantially perpendicular to the tooth's labial surface, said second member having a facial slot formed in an axial-end portion remote from said first member's tooth attachment surface for receiving an arch wire, said second member being freely rotatable on said first member so as to allow sideways rotation of the tooth about said axis when said second member is engaged with an arch wire,
   an arrangement for locking said two members together with a prescribed relative orientation corresponding to the upright position of the tooth so that tipping or uprighting movement of the tooth is prevented when said second member is engaged with the arch wire,
   said second member further comprising
   a cylindrical skirt depending from said axial-end portion, and
   a second slot in said axial end portion which intersects said labial surface and is deeper than said first slot so as to penetrate into said cylindrical skirt in the axial direction, thereby dividing said axial end portion into two parts, and
   said first member further comprising
   a stub axle on which said skirt is slidingly engaged; and
   a first slot in said stub axle which is positioned such that said second slot in said second member and said first slot in said stub axle are aligned in at least one orientation of said first and second members, said second slot and said stub axle slot together being adapted when aligned to receive an arch wire.

2. An orthodontic bracket according to claim 1, said first and second slots in said second member being oriented substantially at 90° relative to one another.

3. An orthodontic bracket according to claim 1, said first member comprising
  a second slot disposed in its tooth attachment surface for receiving accessories.

4. An orthodontic bracket according to claim 3, said first and second slots of the said first member being perpendicularly aligned.

5. An orthodontic bracket for moving teeth, said bracket comprising
  a fixed member for attachment to the labial surface of a tooth, said fixed member having a stub axle formed thereon which is substantially perpendicular to that labial surface when said bracket is mounted on the tooth,
  a rotatable member retained thereon which is freely rotatable about said stub axle, said rotatable member having an axial-end portion that defines a labial surface which is traversed by a first channel in which an arch wire may be seated,
  lock means partially carried by each of said fixed and rotatable members, said lock means functioning to selectively lock said rotatable and fixed members together at a prescribed orientation; and
  said rotatable member further comprising
  a cylindrical skirt depending from said axial end portion, said skirt slidingly engaging said stub axle.

6. An orthodontic bracket as claimed in claim 5, said rotatable member comprising
  a second channel traversing said labial surface, said second channel being oriented at right angles to said first channel, and said second channel penetrating through said axial-end portion and into said cylindrical skirt.

7. An orthodontic bracket as claimed in claim 6, said fixed member comprising
  a third channel formed in said labial surface of said fixed member, said third channel being open to said second channel on said rotatable member, said second and third channels together providing an open slot which can receive an arch wire that acts as a locking member so rotation of both said fixed and rotatable members is prevented.

8. An orthodontic bracket as claimed in claim 7, said fixed member comprising
  a fourth channel formed on said fixed member's lingual surface, said fourth member being perpendicular to said third channel and adapted to receive an uprighting spring or other auxiliary member.

9. A method of moving teeth using an orthodontic bracket as claimed in claim 8, said method comprising the steps of
  attaching said bracket by means of said fixed member to a tooth to be moved
  seating an arch wire in said first channel with said rotatable member being adjusted so that said first channel is aligned with said third channel on said stub axle,
  applying forces to said tooth to tip the tooth along said arch wire,
  removing said arch wire from said first channel,
  turning said rotatable member to re-seat said arch wire in said second channel, and
  applying uprighting forces to said tooth to move it until said second channel is aligned with said third channel so that said arch wire slips therein and locks said fixed and rotatable members to prevent further rotational movement of said tooth.

10. An orthodontic bracket for moving a tooth in situ in consecutive first, second and third phases of treatment, respectively, firstly by tipping, secondly by uprighting, thirdly, by one of edgewise and torquing adjustment, the bracket comprising:
  a first member having a tooth attachment surface for attachment to a tooth's labial surface,
  a second member adapted to receive an arch wire, said second member being mounted on the first member and being freely movable in rotation but only about an axis perpendicular to the said labial surface of the tooth so as to facilitate sideways rotation of the tooth about said perpendicular axis when the member is engaged with the arch wire; and
  means for retaining the second member rotatably on the first member,
  said second member having first and second facial slots formed in an axial-end portion remote from said first member's tooth attachment surface, both said slots being adapted for receiving the arch wire, said first slot receiving the arch wire only in the said axial-end portion, said second slot being disposed at a predetermined angle to the first slot and being deeper than the said first slot so as to cooperate with the said first member to enable the second member to be locked to the first member in a predetermined orientation by means of the arch wire with the latter inserted in the second slot.

11. An orthodontic bracket according to claim 10, said axial-end portion comprising
  a rectangular flange having corners which are adapted for retaining elastic biasing members.

12. An orthodontic bracket for moving teeth, said bracket comprising:
  a fixed member for attachment to the labial surface of a tooth, said fixed member having a stub axle formed thereon which is substantially perpendicular to that labial surface when the bracket is mounted on the tooth,
  a rotatable member retained on the fixed member, being journalled on the stub axle so as to be freely rotatable thereabout, said rotatable member having an axial-end portion that defines a labial surface traversed by first and second channels each adapted to separately receive an arch-wire, said first and second channels having a prescribed facial angular relation and said second channel being deeper than the first channel and cooperating with the fixed member so as to enable said rotatable member to be locked to said fixed member in a predetermined orientation by means of the arch-wire with the latter mounted in the second slot.

13. An orthodontic bracket as claimed in claim 12, said axial-end portion of said rotatable member comprising
  a rectangular flange having corners which are inclined in the lingual direction to provide means for retaining elastic biasing members.

* * * * *